United States Patent [19]

Stonich

[11] 4,265,232
[45] May 5, 1981

[54] INCLINED ARM SUPPORT FOR STROKE VICTIMS

[76] Inventor: Timothy Stonich, 1518 Spencer, Wilmette, Ill. 60091

[21] Appl. No.: 53,966

[22] Filed: Jul. 2, 1979

[51] Int. Cl.³ .................................................. A61F 13/00
[52] U.S. Cl. ......................................... 128/133; 269/328
[58] Field of Search ................ 128/133, DIG. 6, 77, 128/68, 93, 87 R, 85, 89 R; 269/328

[56] References Cited

U.S. PATENT DOCUMENTS

| 432,888 | 7/1890 | Miller | 128/85 |
|---|---|---|---|
| 1,539,911 | 6/1925 | Pendergraft | 128/85 |
| 2,198,908 | 4/1940 | Ellis | 128/85 |
| 2,700,383 | 1/1955 | Moodie | 128/87 R |
| 3,066,322 | 12/1962 | Derby | 269/328 X |
| 3,528,413 | 9/1970 | Aydt | 269/328 X |
| 3,590,817 | 7/1971 | Wresch | 128/133 |
| 3,746,332 | 7/1973 | Hakstian | 269/328 |
| 3,815,588 | 6/1974 | Klausner | 128/77 |
| 3,857,390 | 12/1974 | Harrison | 128/93 |
| 4,082,257 | 4/1978 | Strickland | 269/328 |

*Primary Examiner*—John D. Yasko
*Attorney, Agent, or Firm*—James J. Conlon

[57] ABSTRACT

A portable, light-weight arm support is provided for stroke victims to prop the person's arm at an inclined position to prevent the accumulation of fluids in the hand and wrist area. Arm support surface has a concave contour to comfortably receive a person's arm and includes Velcro straps for holding the arm securely in position. The arm support surface is supported on a pair of spaced legs which have a contoured bottom connector to allow the support to be easily positioned on an irregular surface such as on the arm of a chair or upon a flat surface such as a table.

5 Claims, 6 Drawing Figures

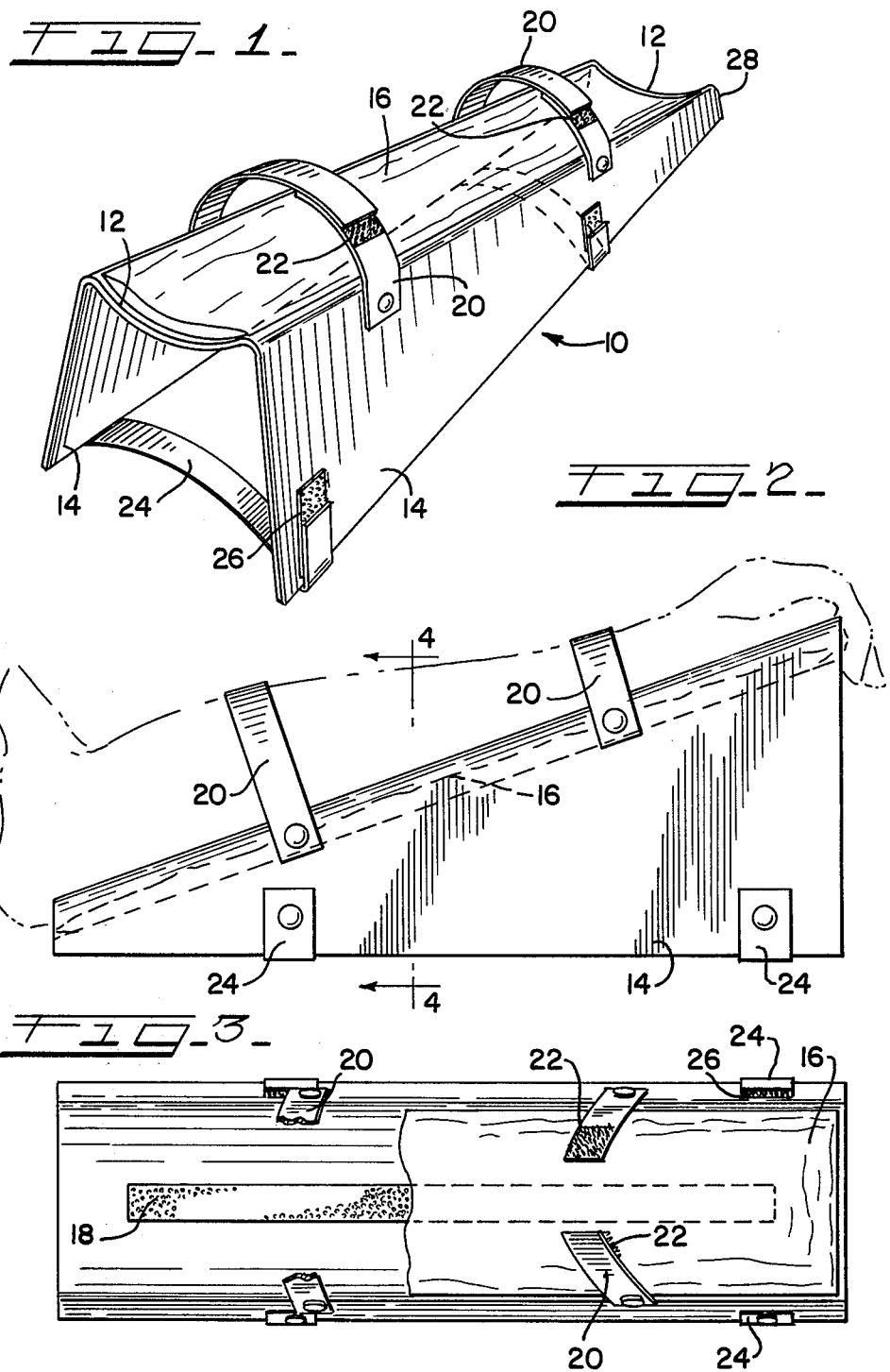

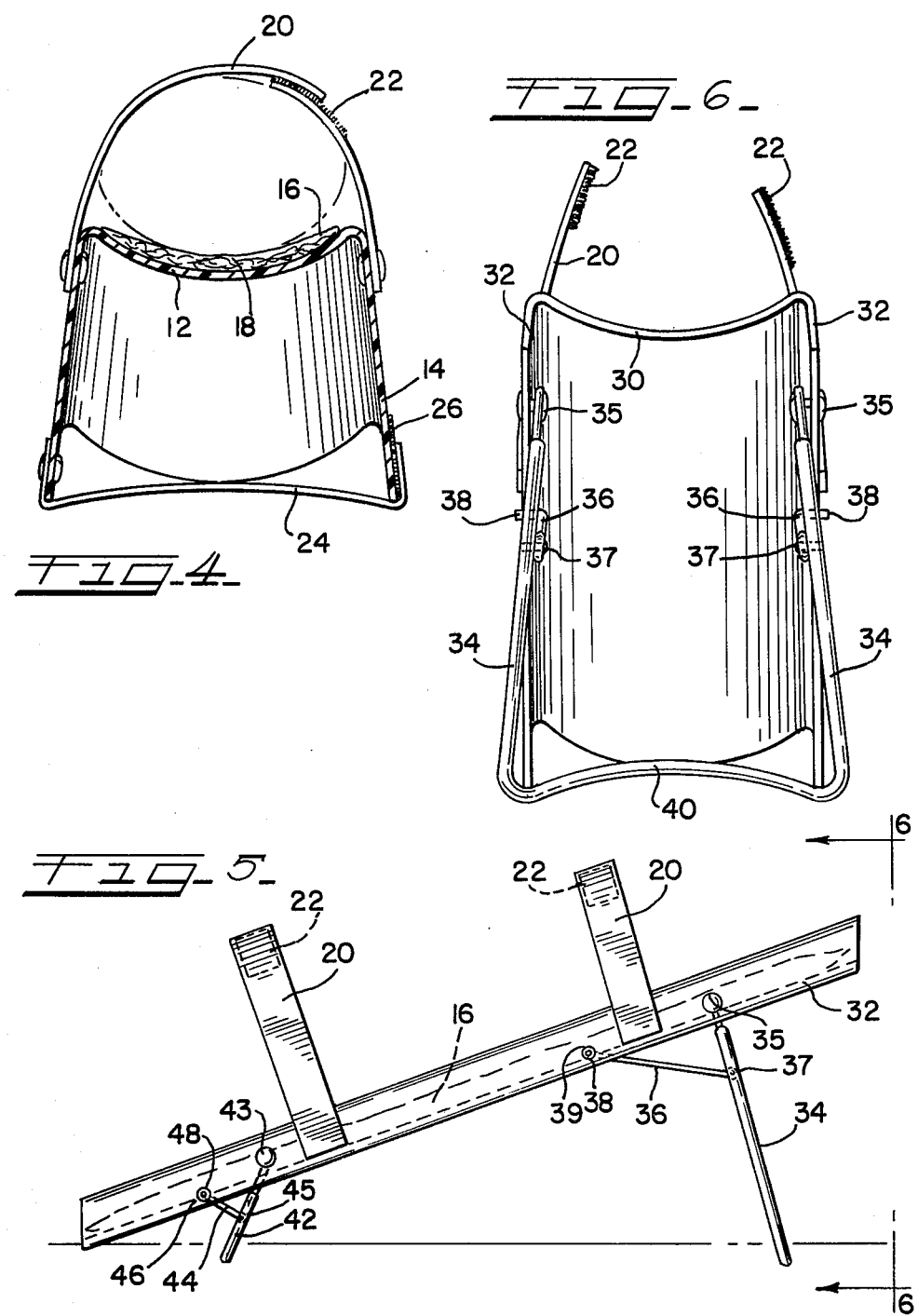

INCLINED ARM SUPPORT FOR STROKE VICTIMS

BACKGROUND OF THE INVENTION (1) Field of the Invention

This invention pertains to an arm support for use by persons who have suffered a stroke. Specifically, an inclined or ramp-type of support is provided which is highly portable and may be supported on a flat surface or on an irregular surface such as the arm rest of a chair or sofa.

(2) Description of the Prior Art

While the prior art shows a number of arrangements for supporting a person's arm during medical treatment such as the contoured arm board disclosed in Hazelwood et al., U.S. Pat. No. 3,295,518 (1968) and in the Eubanks, U.S. Pat. No. 2,630,288 (1953) which shows an adjustable leg rest which may be used to support a person's arm or leg during healing, no device has been found which is specifically aimed at providing a portable ramp type of support for use by stroke victims to prevent the unnatural accumulation of fluids in the hand or wrist area while the person is at rest.

SUMMARY

The nature of this invention is directed to providing a portable yet compact arm rest that may be easily carried, stored and used by stoke victims. Specifically, a hollowed-out ramp member having a contoured arm support surface and a pair of downwardly extending legs depending therefrom may be easily mounted on a table top or on an arm rest by use of the flexible straps or contoured legs and thus, prop up the stroke victim's arm in a slightly raised position. A plurality of bands are provided at each side of the arm rest and are to be connected to hold the wearer's arms securely in position.

One form of the invention provides a shell-type of unit wherein the support legs and contoured arm support surface are a single piece and a pair of straps are mounted at the top of each leg to extend across the contoured surface and be connected to hold the person's arm in place. A second pair of straps are located at the bottom of the support legs and extend across the bottom opening to provide a bottom that will adapt to the contour of many surfaces such as an arm rest, sofa rest, barber's chair, and the like to allow the unit to be used in virtually in any situation.

A modified form of the invention provides a more compact, portable arrangement wherein a contoured arm support surface is provided with a pair of folding legs which mount the arm support surface at an acute angle above the supporting surface and which also include a pair of collapsible folding legs to allow the arm supports to be neatly and compactly folded, transported, and stored by its users. Like the one piece unit, the unit having collapsible legs also includes a pair of straps which extend across the arm support portion and may be connected to hold the wearer's arm in place. It is suggested that Velcro be used on each strap to provide the connecting medium.

It is thus an object of this disclosure to show an arm support for use by stroke victims and which props up the person's arm at an acute angle above horizontal to prevent the unnatural accumulation of fluids which occur in a stroke victim's arms due to restricted circulation.

It is yet another object of this invention to provide an arm support having a contoured arm support surface and upstanding support legs which are interconnected by a contoured member which may adapt to a rounded or non-flat support surface for holding the arm support securely in position.

Another object of this invention is to provide an inclined arm support for use by stroke victims and having a contoured arm support portion having a strip of Velcro attached thereto for the purpose of removably attaching a cushion or arm rest-type of pillow to the arm support surface.

These and other object of the invention will become more apparent to those having ordinary skill in the art with reference to the following description, drawings, and appended claims.

DESCRIPTION OF THE DRAWINGS

FIG. 1 is a pictorial illustration of a single piece forming the arm support disclosed herein;

FIG. 2 is a side elevational view of the arm support illustrated in FIG. 1;

FIG. 3 is a top plan view of the support shown in FIG. 1 with portions of the arm support removed;

FIG. 4 is a sectional view taken generally along the lines 4—4 of FIG. 2;

FIG. 5 is a side elevational view of another form of the invention having collapsible support legs; and FIG. 6 is an end view taken generally along the lines 6—6 of FIG. 5.

DESCRIPTION OF THE PREFERRED EMBODIMENTS

Referring now to the drawings, it is noticed that arm support designated generally by the numeral 10 is provided for use by stroke victims. As it is understood, it is advisable for stroke victims to maintain his or her lower arm and hand in an inclined position to prevent an accumulation of fluids in the hand and wrist area. As it is known, if a stroke affects the right side of an individual's brain, the left portion of that individual's body is affected and vice versa. A certain amount of paralysis, while not dibilitating, may result and cause poor circulation in the extremities and limbs, and in particular, poor circulation at the outer portion such as the hands and wrists. Therefore, stroke victims are generally advised to carry a soft rubber ball which should be squeezed from time to time, not only to improve musculature in the extremity, but also to stimulate circulation. Further, when the stroke victim is sedentary, it is generally advised that he or she maintain the lower arm in a slightly inclined position in order to allow for a natural, gravity-encouraged, flow of fluids throughout the arm to prevent the accumulation of fluids in the hand and wrist areas. To accomplish this inclined positioning, this disclosure provides a contoured, inclined member having an arm support surface which is slightly concaved to fit the contour of the individual's arm. One version of this disclosure provides a one piece, stackable, wedge-shaped support member having a pair of support legs and including a soft, removable pad that fits within the contoured arm support portion. A number of Velcro straps are provided to hold the individual's arm securely in place.

A modification of the above-identified structure is shown in FIGS. 5 and 6 in which a contoured arm support surface is provided with a pair of collapsible, folding legs which fold compactly to the underside of the support surface and thus may be easily stored and transported by the user.

Specifically, FIG. 1 discloses an arm rest designated generally by the numeral 10. Arm rest 10 has a contoured top providing a support surface 12 extending for a width of approximately 4 and ½ inches and having approximately a 1-inch depression between the top ends and the lowest portion at the middle of contoured top 12. This contour provides a comfortable fit for a person's arm and also allow a pillow or cushion 16 to be easily supported on the top 12 and held in place due to the natural contour.

Extending downwardly from the top 12 are a pair of support legs 14 which are spread slightly as they extend downwardly from the top 12 to thus provide more stability to the unit and to allow a plurality of arm rests 12 to be stacked for storage when used on a large scale in a hospital or rehabilitation institute. Cushion 16 may be located in the contoured top 12 and held in place by a strip of Velcro designated at 18. Velcro is a commonly recognized and known trademark of the Velcro Corporation and the type of Velcro utilized is that disclosed in the De Mestral U.S. Pat. No. 2,717,437 which is incorporated by reference herein.

As shown in FIGS. 1–4, a pair of top straps 20 are attached to each side 14 and extend across the top 12. Each strap terminates with an attachment of Velcro designated at 22. Velcro is suggested to be used in this application because it is soft, flexible, easily cleaned and can adapt to different dimensions and sizes of individual's arms and may be easily connected and disconnected.

As shown in the illustrations, at least two straps 24 extend across the bottom of the arm rest 10 and interconnect the bottom portions of the spaced support legs 14. Like the top straps 20, the bottom straps 24 utilize Velcro 26 as the means for connecting the straps 24 to the support legs 14. Bottom straps 24 are flexible members and the length of Velcro 26 is provided to allow the amount of slack in the bottom straps 24 to be adjusted and thus conform to the contour of a supporting article such as an arm rest on a chair, sofa, or the like.

As shown in FIGS. 1–4, the arm rest 10 provides an inclined ramp. It is suggested or estimated that the length of the ramp would be approximately 18 to 20 inches and provide an angle of approximately 20° for elevating the victim's arm.

The shell version described above provides a compact, portable unit which may be easily transported and because of the diverging support legs can be easily stacked and stored in a hospital or rehabilitation center or the like without consuming an inordinate amount of space. Because a suggested material is lightweight aluminum, fiberglass or a thermoset-type of plastic material which could be cleaned with high temperature water without damaging the material, the unit may be easily transported, stored, and cleaned.

A modified form of this disclosure is illustrated in FIGS. 5 and 6 wherein a similar type of unit provides a contoured top 30 having the same dimensions of the above described top but not having the depending, diverging, integral support legs 14, but being provided with collapsible support legs which can be stored on the underside of the top 30 to reduce size for ease of transport and require less storage room for the unit. Specifically, a contoured top is designated 30 and includes a pair of depending, shortened sides 32 extending therefrom. A front leg 34 extends downwardly from the top 30 and is attached to the sides 32 with a pivot or hinge pin designated 35. A brace 36 is privotally attached to front leg 34 and extends outwardly therefrom. The brace 36 includes a locking finger 38 which extends at right angles to the brace 36 and cooperates with openings 39 in the sides 32. Thus, it is noticed that the brace 36 may be disconnected from the sides 32 by merely bending the brace 36 inwardly intil the finger 38 clears the opening 39 at which time the front legs 34 may be folded to the underside of the top 30. As shown in FIG. 6, a so-called contoured connector 40 interconnects each side leg 34 and allows the unit to be easily mounted on a flat or contoured surface.

A rear leg support, like the front leg support, is illustrated in FIG. 5. The rear leg 42 is pivotally attached to the sides 32 and extends downwardly therefrom in a direction opposite the direction of the extension of the front legs 34. Rear legs 42 are pivotally attached to sides 32 with a hinge pin 43 and include a support bracket 44 extending therefrom. Support bracket 44 is pivoted to the legs 42 at 45, and, like the front legs 34, bracket 36 includes a locking finger 46 which cooperates with an opening 48 and the side 32. To disconnect or to fold the rear legs 42 the brace 44 is pushed inwardly of the sides allowing the locking finger 46 to clear its associated locking opening 48 at which time the legs 42 are folded or moved clockwise as shown in FIG. 5 to the underside of the top 30. A pair of arm straps 22 and associated Velcro-type locking arrangement 22 are utilized to hold the user's arm in place on the top 30.

Thus, it has been shown by the foregoing that the arm rest disclosed herein provides a much needed implement for use by stroke victims which allows them to be comfortable when in a sedentary position such as when watching television or at a movie. The arm rest of this disclosure props up a person's arm in a natural 20° angle to prevent the accumulation of fluids therein. By providing bottom members which are contoured, the support can adapt itself to various contour support surfaces The foregoing description and drawings merely explain and illustrate the invention and the invention is not limited thereto, except insofar as the appended claims are so limited, as those who are skilled in the art and have the disclosure before them will be able to make modifications and variations therein without departing from the scope of the invention.

I claim:

1. A portable arm rest adapted to be easily transported and carried by stroke victims to position the user's forearm in a position with the hand elevated above the elbow to prevent the accumulation of fluids in the hand and wrist area and the portable arm rest being adapted for mounting and positioning upon a stationary object such as a table, arm of a chair or the like, the improvement comprising:
   an arm support section adapted to receive the stroke victim's forearm and position the person's hand above his or her elbow;
   said arm support section having a concave curvature providing a dish-shaped cross section having sides located above a lower, central portion;
   said arm support having a length less than twenty inches to support a person's forearm and receive the elbow and hand along the length of the support;
   support legs extending from the contoured support section and having means adapted to dispose the arm support section at an acute angle of at least twenty degrees above horizontal;

connecting means extending across the bottom of the support legs and providing means adapted to support the unit on a flat, horizontal surface as well as on a contoured or irregular surface;

arm support straps extending from side to side atop the contoured arm support section and providing a first strap adapted to secure the user's wrist and a second strap to secure the forearm area near the user's elbow;

said support legs having means for easily storing a plurality of arm rests in a compact configuration.

2. The portable arm rest of claim 1 wherein said support legs include:

collapsible legs extending downwardly from the contoured top and having hinged, pivot means attaching legs to the arm rest;

locking means for holding the support legs in supporting position extending from the underside of the contoured arm support;

said locking means having movable locking fingers adapted to engage the arm support section for locking the support legs.

3. The arm support of claim 1 wherein said support legs includes:

side legs comprising an integral extension of the arm support and providing a one-piece construction;

said side legs providing means diverging downwardly and outwardly from the arm support section to thereby allow a plurality of arm rests to be stacked upon one another.

4. The portabe arm rest of claim 1, and:

said arm support section including a removable cushion means located theron to provide a soft support surface for a user's forearm, and, said cushion having means extending the length of the dish-shaped cross section;

connecting means attached to the arm support section;

mating means attached to the underside of the cushion for connecting with the connecting means to hold the cushion in place.

5. The arm rest of claim 1 wherein said connecting means and mating means include:

Velcro fabric.

* * * * *